United States Patent [19]

Brillhart et al.

[11] Patent Number: 5,303,306

[45] Date of Patent: Apr. 12, 1994

[54] HEARING AID WITH PROGRAMMABLE REMOTE AND METHOD OF DERIVING SETTINGS FOR CONFIGURING THE HEARING AID

[75] Inventors: Bruce A. Brillhart; Theodore P. Adams, both of Edina, Minn.

[73] Assignee: AudioScience, Inc., Minnetonka, Minn.

[21] Appl. No.: 796,659

[22] Filed: Nov. 25, 1991

Related U.S. Application Data

[63] Continuation of Ser. No. 362,827, Jun. 6, 1989, abandoned.

[51] Int. Cl.⁵ .................................. H04R 25/00
[52] U.S. Cl. ................................. 381/68; 381/68.2; 381/68.4
[58] Field of Search ............... 381/68, 68.1, 68.2, 381/68.3, 68.4, 60; 128/746

[56] References Cited

U.S. PATENT DOCUMENTS

| | | |
|---|---|---|
| 2,390,794 | 12/1945 | Knight ........................... 381/68.4 |
| 3,193,048 | 7/1965 | Kohler . |
| 3,209,081 | 9/1965 | Durote et al. ................... 3181/68 |
| 3,385,937 | 5/1968 | Lafon . |
| 3,571,529 | 3/1972 | Gharib . |
| 3,989,904 | 11/1976 | Rohrer et al. . |
| 4,006,321 | 2/1977 | Carlson . |
| 4,051,330 | 4/1977 | Cole . |
| 4,063,034 | 12/1977 | Peters . |
| 4,118,604 | 10/1978 | Yanick ........................... 381/68 |
| 4,119,814 | 10/1978 | Harless .......................... 381/68 |
| 4,149,032 | 4/1979 | Peters . |
| 4,170,720 | 10/1979 | Killion . |
| 4,187,413 | 2/1980 | Moser . |
| 4,232,679 | 11/1980 | Schulman . |
| 4,366,349 | 12/1982 | Adelman . |
| 4,393,275 | 7/1983 | Feldman et al. ................ 381/68.2 |
| 4,396,806 | 8/1983 | Anderson . |
| 4,417,102 | 11/1983 | Allen . |
| 4,425,481 | 1/1984 | Mansgold et al. ............. 381/68 |
| 4,442,540 | 4/1984 | Allen . |
| 4,466,119 | 8/1984 | Peter et al. . |
| 4,471,171 | 9/1984 | Kopk et al. . |
| 4,484,345 | 11/1984 | Stearns . |
| 4,508,940 | 4/1985 | Steeger . |
| 4,577,641 | 3/1986 | Hochmair et al. ............. 128/746 |
| 4,592,087 | 5/1986 | Killion . |
| 4,596,902 | 6/1986 | Gilman . |
| 4,613,937 | 9/1986 | Batty, Jr. . |
| 4,622,440 | 11/1986 | Slavin . |
| 4,622,692 | 11/1986 | Cole . |
| 4,628,529 | 12/1986 | Borth et al. . |
| 4,677,675 | 6/1987 | Killion et al. . |
| 4,677,679 | 6/1987 | Killion . |

(List continued on next page.)

FOREIGN PATENT DOCUMENTS

| | | | |
|---|---|---|---|
| 0064042 | 11/1982 | European Pat. Off. ............. 381/68 |
| 3527112 | 1/1987 | Fed. Rep. of Germany ........ 381/68 |
| 3642828 | 8/1987 | Fed. Rep. of Germany ........ 381/68 |
| 0670349 | 5/1989 | Switzerland .......................... 381/68 |

OTHER PUBLICATIONS

Two brochures for the Zeta Noise Blocker.
A brochure for the Faro Instrument.
A brochure for the Quattro device.

(List continued on next page.)

Primary Examiner—Curtis Kuntz
Assistant Examiner—J. Chan
Attorney, Agent, or Firm—Vidas, Arrett & Steinkraus

[57] ABSTRACT

A hearing aid is provided which is controlled by a remote control via infrared radiation. The remote control is provided with volume control keys, standardized sound environment keys and custom sound environment keys. When one of these keys is pressed, new circuit settings are transmitted to the hearing aid via infrared radiation. An audiologist tests a patient to obtain an audiogram, MCL and LDL measurements. A set of template overlays is used to determine curve shape and magnitude of loss. This data is stored in the remote control which uses it to derive the circuit settings. These settings which constitute a baseline set of settings are modified as a result of a key on the remote control being pressed.

19 Claims, 6 Drawing Sheets

U.S. PATENT DOCUMENTS

| | | |
|---|---|---|
| 4,680,798 | 7/1987 | Neumann . |
| 4,689,819 | 8/1987 | Killion . |
| 4,689,820 | 8/1987 | Kopke et al. . |
| 4,718,099 | 1/1988 | Hotvet . |
| 4,719,430 | 1/1988 | Cole . |
| 4,731,850 | 3/1988 | Levitt et al. . |
| 4,750,207 | 6/1988 | Gebent et al. . |
| 4,763,753 | 8/1988 | Killion . |
| 4,790,019 | 12/1988 | Hueber . |
| 4,791,672 | 12/1988 | Nunley . |
| 4,845,755 | 7/1989 | Busch et al. ............... 381/68 |
| 4,846,180 | 7/1989 | Buffet . |
| 4,879,749 | 11/1989 | Levitt et al. ............ 381/68.4 |
| 4,887,299 | 12/1989 | Cummins et al. ......... 381/68.4 |
| 4,918,736 | 4/1990 | Bordowijk ................. 381/68 |
| 4,918,737 | 4/1990 | Luethi ....................... 381/68 |
| 4,920,570 | 4/1990 | West et al. ................ 381/68 |
| 4,941,179 | 7/1990 | Bergenstaff et al. ....... 381/68.4 |
| 4,947,432 | 8/1991 | Topholm .................. 381/68.2 |
| 4,953,112 | 8/1990 | Widin et al. . |

OTHER PUBLICATIONS

A brochure for the Phox device.

An article entitled "The Rechargeable Hearing Instrument System", by Toni titles et al., *Hearing Instruments* vol. 38, No. 7, (1987).

An article entitled "Fitting A Programmable Hearing Instrument", by W. Widin et al., Hearing Instruments, vol. 39, No. 6 (1988).

An article entitled "Full Dynamic Range Multiband Compression In a Hearing Aid", by F. Waldauer et al., *The Hearing Journal,* Sep. 88.

An article entitled "Clinical Measurement of Loudness Growth", by Vincent Pluvinage, *Hearing Instruments,* vol. 30, No. 3, (1989).

Chapter 8 from *Handbook of Hearing Aid Amplification,* vol. I: "Theoretical and Technical Consideration", College Hill Press, 1988.

An article entitled "Filtering System Discriminates Between Noise & Speech", *Design News,* pp. 204–206 (Nov. 23, 1987).

An article entitled "Digital Hearing Aids", ASHA, pp. 45–47, Sep. 1987.

An article entitled "A Self-adaptive noise filtering system", *Hearing Instrument,* vol. 37, No. 9, (1986).

An article entitled, "Latest Devices Aid Severe Cases of Hearing Loss", Wall Street Journal, Mar. 23, 1988.

A packet of information on the Zeta Noise Blocker dated Oct. 1987.

An article entitled "Current Audiologic Practices in the United States", *The Hearing Journal,* Apr. 1989.

"Programmable Hearing Aid with Multichannel Compression", by S. Mangold and A. Leijon, Scan Audiol 8:121–126, 1979.

"Programmable Hearing Aid", by Stephen Mangold, Research Laboratory of Electronsc Chalmers Univer of Tech, Goteberg Sweden.

"The Amplifier As the Heart of the Hearing Aid", by R. A. Gibbons & W. A. Cole Hearing Instruments, vol. 32, No. 4, 1981.

"Digital Hearing Aids: A Tutorial Review", by Harry Levitt, Veterans Administration, Journal of Rehabilitation Res. & Dev. vol. 24, No. 4.

"A Digital Master Hearing Aid", by Harry Levitt, Veterans Administration, Journal of Rehabilitation Research and Devl. vol. 23, No. 1.

HEARING AID WITH PROGRAMMABLE REMOTE AND METHOD OF DERIVING SETTINGS FOR CONFIGURING THE HEARING AID

This is a continuation of copending application Ser. No. 07/362,827 filed on Jun. 6, 1989, now abandoned.

BACKGROUND OF THE INVENTION

1. Field of the Invention

This invention generally relates to hearing aids. More specifically, this invention relates to a hearing aid with a programmable remote control, and the method of deriving settings to configure the hearing aid.

2. Description of the Related Art

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

A brochure for the ZETA NOISE BLOCKER made by Intellitech Corp. of Northbrook Ill., is directed to a unit which processes sound in real time with an onboard microcomputer. This unit sends the actual filtered sound to the hearing aids with a small delay. This is different from the present invention in that applicant's invention sends settings to the hearing aid to configure the filters in the hearing aid. This reference is not considered anticipatory or suggestive of the invention.

A brochure for the FARO instrument made by Philips, is directed to an infrared remote control device. However, this unit does not send the entire prescription to the hearing aid, but instead sends a signal which sets the hearing aid to one of series of settings stored in the hearing aid. Therefore, this device in not considered anticipatory of the invention, nor is the overall concept of the invention suggested by this reference.

An article entitled "The Rechargeable Hearing Instrument System" by Toni Gitles et al, *Hearing Instruments*, Vol. 38, No. 7 (1987), is directed to a rechargeable hearing aid system. While this reference is considered relevant to the rechargeable battery portion of the present invention, it is not considered anticipatory or suggestive of the invention.

A brochure for QUATTRO made by Widex Hearing Aid Co. Inc. of Long Island City, N.Y., is directed to a radio wave remote which sends a signal allowing the hearing aid to switch between four on board settings. This brochure is not considered anticipatory or suggestive of the invention.

An article entitled "Fitting A Programmable Hearing Instrument" by G. Widin et al, *Hearing Instruments*, Vol. 39, No. 6 (1988) describing the 3M MemoryMate is directed to a hearing aid which allows the user to manually switch between eight settings stored in the actual hearing aid. Since the settings are stored on board this reference is not considered anticipatory or suggestive of the invention.

A brochure for the PHOX made by Bernafon, Inc. is directed to a unit which is used by the Audiologist to configure the hearing aid. The unit is used to store prescriptions on board the hearing aid and is therefore not considered anticipatory or suggestive of the invention.

An article entitled "Full Dynamic Range Multiband Compression In a Hearing Aid" by Fred Waldhauer & Edgar Villchur, *The Hearing Journal*, Sep. 1988, relates to dynamic range compression.

An article entitled "Clinical Measurement Of Loudness Growth" by Vincent Pluvinage, *Hearing Instruments*, Vol. 40, No. 3 (1989), relates to MCL and LDL.

Chapter 8 from *Handbook of Hearing Aid Amplification*, Vol. I: "Theoretical and Technical Consideration", College Hill Press, 1988, relates to the formulas used to determine hearing aid circuit settings.

U.S. Pat. No. 4,425,481 entitled "Programmable Signal Processing Device" issued to Mansgold is directed to a hearing aid with several different settings for configuring the hearing aid for different environments. The settings are polled sequentially via up or down switches which roll up or down to the next setting. Because the settings are stored on board the hearing aid and not sent via infrared radiation from a remote control this device is not considered anticipatory or suggestive of the invention.

U.S. Pat. No. 4,471,171 entitled "Digital Hearing Aid And Method" issued to Kopke is directed to a hearing aid which stores the user setting on board the hearing aid. The setting is in the form of a transfer function which is stored in EEPROM or EARAM. A test program is stored in ROM. Running the test program allows the user to modify the transfer function stored in the EEPROM or the EARAM. This device does not use a remote control to send new settings to the hearing aid, but instead relies on the user to reprogram the unit themselves. Therefore, this reference is not considered anticipatory or suggestive of the invention.

U.S. Pat. No. 4,596,902 entitled "Processor Controlled Ear Responsive Hearing Aid And Method" issued to Gilman is directed to a hearing aid controlled by a microprocessor and a feedback microphone in the ear canal. The hearing aid has several sets of instructions stored on board. Using the feedback microphone the microprocessor monitors the ear canal and automatically switches settings. The reference also teaches manual control of the hearing aid. Since the settings are stored on board the hearing aid and not sent via infrared radiation this device is not considered anticipatory or suggestive of the invention.

U.S. Pat. No. 4,622,440 entitled "Differential Hearing Aid With Programmable Frequency Response" issued to Slavin is directed to a hearing aid which provides for user adjustments via manual controls. This reference is not considered anticipatory or suggestive of the invention.

U.S. Pat. No. 4,680,798 entitled "Audio Signal Processing Circuit For Use In A Hearing Aid And Method For Operating Same" issued to Neumann is directed to a hearing aid which splits the audio signal into a plurality of frequency bandwidths, separately amplifying each bandwidth, then summing back to a single signal for output. Data are stored on board for use by a microprocessor to aid in setting the settings of each of the amplifiers. The settings are determined on board, therefore, this reference is not considered anticipatory or suggestive of the invention.

U.S. Pat. No. 4,731,850 entitled "Programmable Digital Hearing Aid System" issued to Levitt is directed to a hearing aid which stores various filter coefficients in an EEPROM on board the hearing aid. These settings are loaded into the EEPROM with a computer by an Audiologist. Since the settings cannot be loaded into memory via a remote control by the user and are stored on board the hearing aid this reference is not considered anticipatory or suggestive of the invention.

SUMMARY OF THE INVENTION

Many of the references discussed above store several settings for the hearing aid on board the hearing aid itself. This requires a larger or more complex hearing aid than applicant's hearing aid, because all of the available settings for applicant's hearing aid are stored in the remote control.

Once an Audiologist tests the patient and prepares a standard pure tone air conduction audiogram, the audiologist matches the shape of the audiogram curve to a a set of template overlays. Another set of template overlays is used to determine the magnitude of the hearing loss. The audiologist also measures the "most comfortable loudness" level (MCL) and the "loudness discomfort level" (LDL) to complete the minimum required testing procedures. The testing procedures used to 13 determine the MCL and the LDL vary from Audiologist to Audiologist, but are well known in the art. These tests provide the data needed to derive a set of baseline settings for each ear.

The results of the tests (audiogram curve shape, magnitude of loss, MCL and LDL) are entered into the remote control by the audiologist. Settings may be stored for one or both ears. These test results are used by the remote control to generate the baseline settings or circuit settings for the ear or each ear as the case may require. The baseline settings may be different for each ear depending on the asymmetry of hearing loss of each ear. These baseline settings or circuit settings consist of the filter break frequencies, the break slopes, the relative gain between the high frequency and low frequency amplifiers, the maximum power output, and the dynamic range compression constant.

These baseline settings can be modified by the patient by means of the keys on the remote control. These keys correspond to different sound environment conditions, including but not limited to: automobile; fan; phone; television; music; voice; and restaurant. In addition to these standard environmental sound conditions several keys are programmed for custom environments that the patient may find themselves in, for example, the work sound environment. Volume controls are also contained on the remote control. The advantage of using the remote control to control the hearing aid response, as opposed to placing these controls on the hearing aid itself, is that the resulting hearing aid is less prone to damage and breakdown. Also, this allows the hearing aid to be simpler and smaller and have a much higher reliability. Since the controls are supplied on the remote control instead of being located on the much smaller hearing aid, more controls may be provided. Also, by allowing the audiologist to program the remote control, the audiologist is provided with maximum flexibility in providing a prescription for a patient.

Once the patient pushes a key on the remote control a computer program contained therein modifies the baseline settings for the sound environment indicated and sends the new settings to the hearing aid via a series of coded infrared radiation pulses.

BRIEF DESCRIPTION OF THE DRAWINGS

A detailed description of the invention is hereafter described with specific reference being made to the drawings in which.

DESCRIPTION OF THE PREFERRED EMBODIMENTS

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

Figure 1:
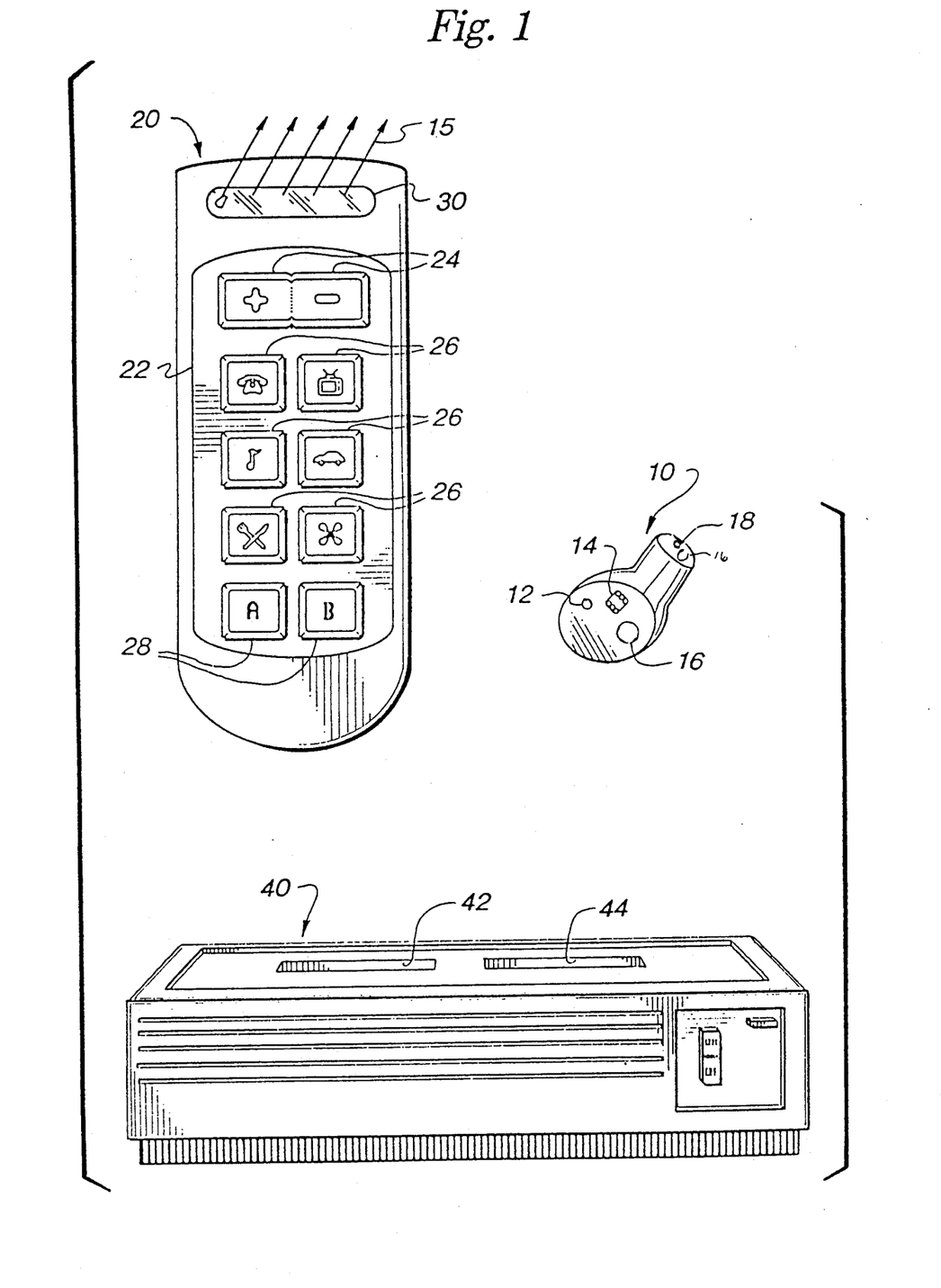
FIG. 1 is a diagram showing components of the system: the hearing aid, the remote control, and a charger unit.

Referring now to FIG. 1, a hearing aid is shown generally at 10. The hearing aid 10 is of a standard shape and plastic material as is already known in the art and has a microphone 12 for receiving sound and converting it into an electrical signal. It also includes an infrared radiation sensor 14 for receiving a signal 15 sent from the remote control, shown generally at 20; a vent 16, and a speaker 18 (also known as a receiver in the art) which converts a signal processed by the hearing aid into sound and directs it into the ear. The circuit connected between microphone 12 and the speaker 18 is discussed with reference to FIG. 3. The hearing aid 10 is powered by a rechargeable battery (not shown) which may be nickle-cadmium, lithium, or any other type of rechargeable battery.

Remote control 20 is designed to fit comfortably into the hand of a patient and may take various configuration, one of which is shown. The remote control allows the patient to modify the settings of the circuitry inside the left ear or right ear hearing aid by depressing a key on the keypad 22. The keypad 22 consists of a pair of volume control keys 24, standard sound environmental keys 26, and a pair of custom sound environmental keys 28. The volume control keys 24 consist of one key which raises the volume by a predetermined amount, between 2 and 5 dB in the preferred embodiment, and another key which lowers the volume by the same predetermined amount. The keys indicated at 26 activate a computer program in the remote control which configures the circuitry of a selected hearing aid to different circuit settings, as may be appropriate for different sound environments, by changing the values of the filter break frequencies, the break slopes, the relative gain between the high and low frequency amplifiers, the maximum power output, and the dynamic range compression constant, as will be discussed below. These sound environments may include, but are not limited to, the following: automobile; fan; phone; television; music, voice, and restaurant, and are denoted by an appropriate graphical symbol on the key. Finally, reference numeral 28 indicates a pair of special custom environmental keys, although provision may be made for more than two custom keys. The custom key might represent the sound environment of a patient with special needs such as at work, for example. The infrared radiation directional panel is shown at 30 and is designed to transmit infrared radiation substantially perpendicular to the face of the remote control. Panel 30 may be canted at an angle to the face of the remote control 20. This allows the patient to hold the remote comfortably in their hand and still direct the infrared radiation towards the hearing aid in the patient's ear. Although infrared radiation is preferred for transmission, any other form of transmittable radiation may be used. The remote control may also contain a switch that would allow the patient to set the remote control 20 to control either the right or left ear hearing aid (not shown). Alternatively, it is also contemplated that both sets of baseline settings may be transmitted to both hearing aids, with appropriate circuitry contained in the hearing aids to determine which settings to use to configure the hearing aid. Of course, if only one hearing aid is required for a particular patient then neither the switch nor the transmission of both sets of settings is required.

A recharger for the batteries (not shown) contained in the hearing aids is shown generally at 40. The recharger 40 is inductively coupled to the batteries to recharge the batteries when the hearing aids are placed in the cups 42 and 44. Rechargers such as 40 are well known in the art and are discussed in the article cited above. Recharger 40 may be supplied with either one or two cups. Recharger 40 may be used to recharge either Nickle-Cadmimum batteries, lithium batteries or any other rechargeable type of battery.

Figure 2:
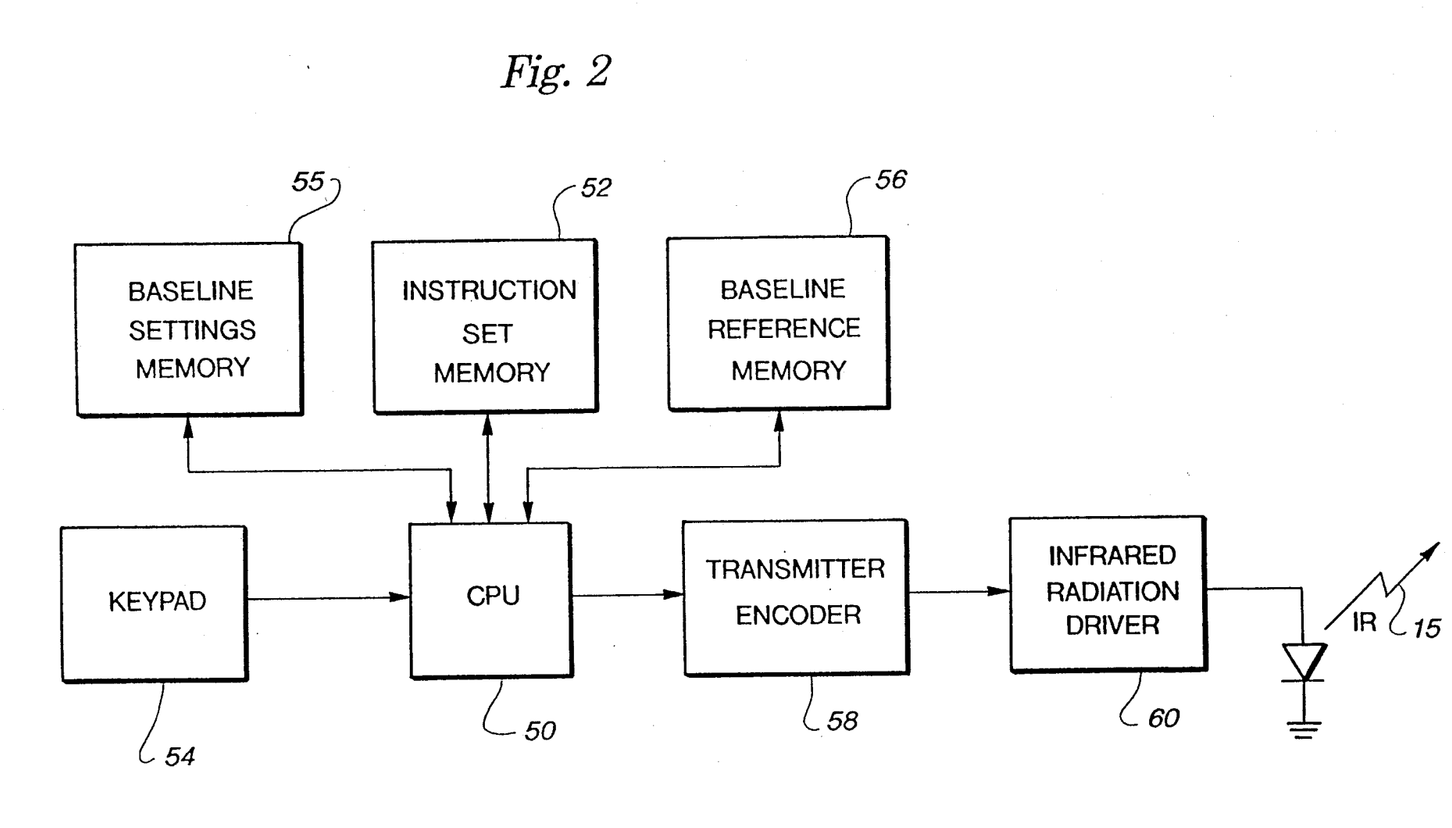
FIG. 2 is a block diagram of the remote control.

Referring now to FIG. 2, a processor 50, which is a microprocessor in the preferred embodiment, is controlled by a set of instructions stored in memory 52. The set of instructions stored in memory 52 comprises a computer program which monitors the keypad 54 to determine if a key has been pressed, then executes the appropriate computer program instructions for that key. The patient's baseline reference data are stored in memory 56. Memory 56 may store the data for one or both ears. The patient's actual baseline settings, which are the data values used to configure the filter break frequencies, the break slopes, the relative gain between the high and low frequency amplifiers, the maximum power output, and the dynamic range compression constant, are stored in memory 55 or derived by means of a formula stored in memory 52. Memories 52, 55 and 56 may be any type of conventional memory, including but not limited. to, RAM; ROM; EPROM; EEPROM; PROM; FRAM, or a set of dip switches. In the preferred embodiment memory 52 is ROM while memory 56 consists of one or more sets of dip switches which act as data inputs to a formula which is used to derive the baseline settings referred to at 55.

The actual baseline settings can be derived in several ways. They may be determined by means of a lookup table, which may be stored in either memory 55 or memory 52. Alternatively, the baseline settings may be derived from several standard formulas as discussed in the *Handbook of Hearing Aid Amplification*, cited above. Many different standard formulas may be stored in the remote control. The dip switch settings in memory 56 specify which type of formula to use. The dip switch settings for audiogram curve shape, magnitude of loss, MCL, LDL, etc. are data inputs to the formula. With these inputs the formula provides values for the filter break frequencies, the break slopes, the relative gain between the high and low frequency amplifiers, the maximum power output, and the dynamic range compression constant, which specify the response of hearing aid at different frequencies. The resulting baseline settings are then stored in memory 55. Examples of the standard formulas which may be stored on board the remote control 20 are POGO (Prescription of Gain/Output) and NAL (National Acoustics Laboratory), although others may be stored. A custom formula may also be entered into the remote controls memory by either connecting the remote control 20 directly to an input device such as a computer keyboard, or by providing a switch or using a keypad key sequence to place the remote control into program mode, then using the keypad keys to enter the custom formula. The dip switch settings in memory 56 would indicate that a custom formula was to be used. Finally, the actual settings themselves may be entered directly into memory 55, either by using an input device or by placing the remote control into program mode and using the keypad keys to input the baseline settings.

In operation, the baseline settings, or the baseline settings as modified by the program stored in memory 52 in response to a key being pressed on keypad 54, are encoded by the transmitter encoder 58, then transmitted to the hearing aid as a series of infrared radiation pulses 15 by the infrared radiation driver 60.

Any one of several workable programs to control the remote control may be designed and used herein and will be readily achievable by those of ordinary skill in the art.

Figure 3:
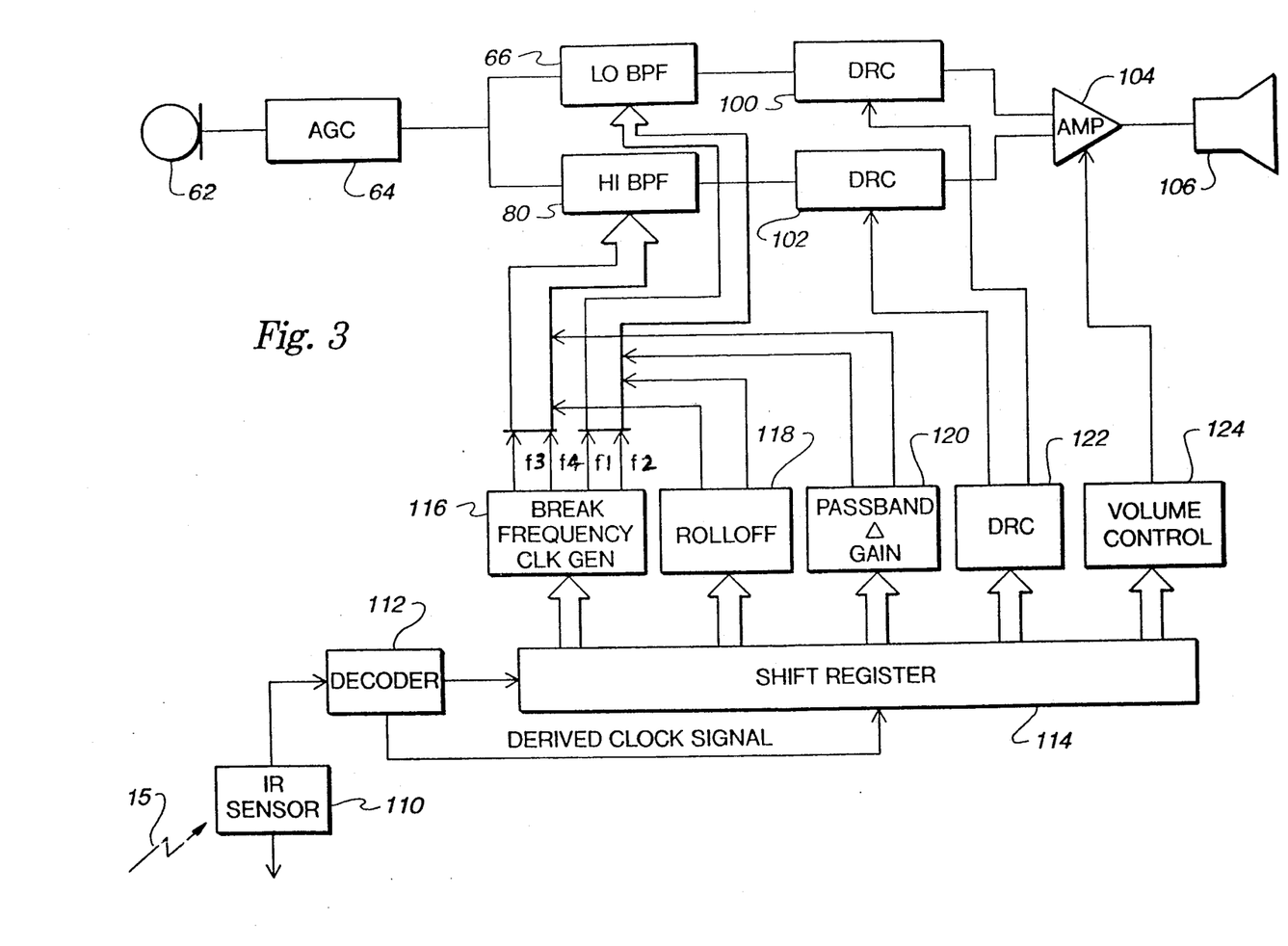
FIG. 3 is a block diagram of the hearing aid.
Figure 4:
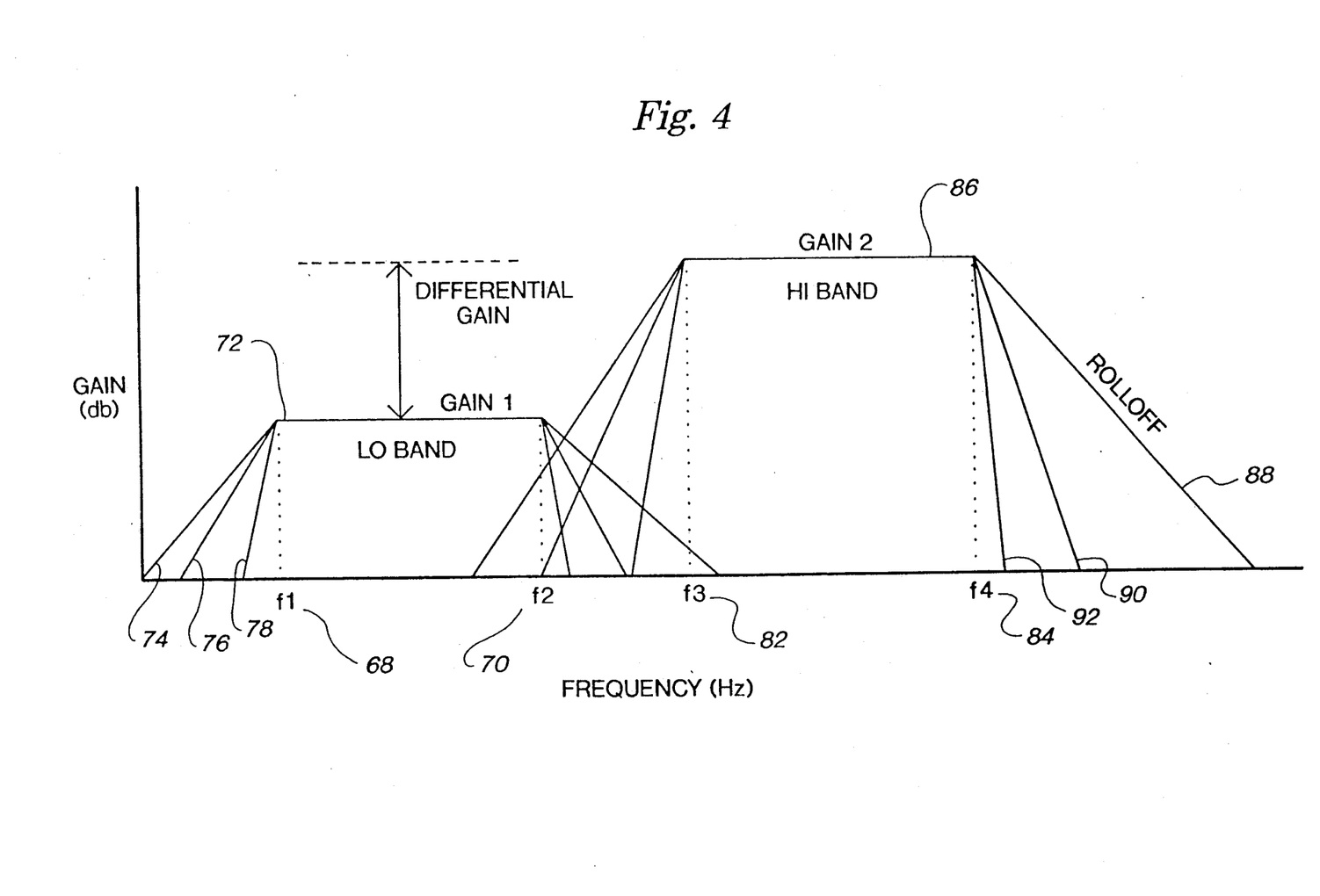
FIG. 4 is a graph of gain vs. frequency of the hearing aid amplifier circuit.

Referring now to FIGS. 3 and 4 together, microphone 62 receives sound, converts it to an electrical signal and feeds the electrical signal to an analog amplifier as is well known in the art. The amplifier of the preferred embodiment consists of an automatic gain control 64 (AGC) which prevents saturation of the amplifier and thereby prevents distortion caused by loud noises. The AGC 64 is connected to a low frequency bandpass filter 66 which amplifies signals between $f_1$ and $f_2$, shown respectively at 68 and 70 in FIG. 4, to $gain_1$ shown at 72 in FIG. 4. Examples of one, two or three pole rolloff are shown in FIG. 4 at 74, 76, and 78, although it is contemplated that more than three poles may be used. The particular values of $f_1$, $f_2$, $gain_1$ and the rolloff are determined by the data transmitted by remote control 20.

The AGC 64 is also connected to a high frequency bandpass filter 80 which amplifies signals between $f_3$ and $f_4$ to a value of $gain_2$, shown respectively in FIG. 4 at 82, 84, and 86. The possible rolloff characteristics are shown at 88, 90 and 92, corresponding to a one, two or three pole rolloff, although it is contemplated that more than three poles may be used. The design and use of filters similar to 66 and 80 are well known in the art. The output of filters 66 and 80 are connected to dynamic range compression circuits 100 and 102. The design and use of dynamic range compression circuits similar to 100 and 102 are well known in the art and are discussed in U.S. Pat. No. 4,170,720. The output of circuits 100 and 102 are connected to amplifier 104 which in turn is connected to speaker 106 (also known as a receiver). The amplifier 104 controls the volume of the sound made by speaker 106.

The lower portion of FIG. 3 is a digital control circuit which receives the data transmitted as a series of infrared radiation pulses 15 by the remote control 20, decodes this data and through control circuitry configures the analog portion of FIG. 3. The remote control 20 transmits a predetermined number of bursts of infrared radiation 15 which are spaced apart in time to sychronize the receiver with the transmitter. The receiver 110 is connected to decoder 112 which uses these sychronizing bursts to determine when the sensor 110 should sample the output of the remote control 20. If the sensor 110 samples, and receives a burst of infrared radiation a digital 1 is passed into the shift register 114. If the sensor 110 samples and does not receive a burst of infrared radiation, a digital 0 is passed into the shift register 114. This is amplitude modulated coding, but it is contemplated that phase or frequency modulated coding may be used as well. The sychronizing bursts also contain start and stop information indicating when the transmission starts and ends, as is well known in the art. Once all the 1's or 0's have been loaded into the shift register these values are passed through to the connected digital control circuit elements 116, 118, 120, 122, and 124. The break frequency clock generator is shown at 116; the rolloff control is shown at 118; the passband gain is shown at 120; the dynamic range compression control is shown at 122, and the volume control is shown at 124. The design of these types of control circuits is well known in the art. The ultimate result is that the signal from microphone 62 is processed according to the transfer characteristics in FIG. 4 and is output through speaker 106 as sound which is directed into the ear channel.

Figure 5:
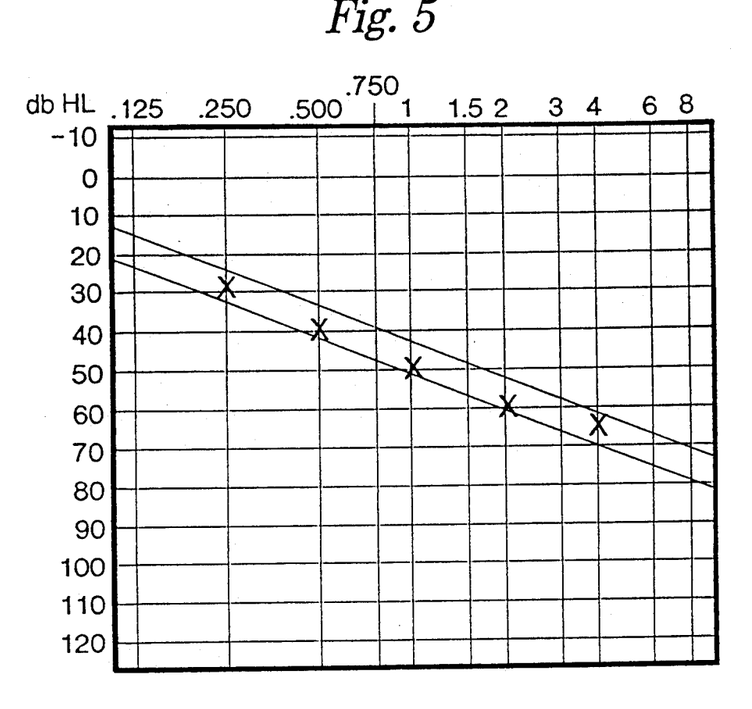
FIG. 5 is an audiogram of an exemplary patients ear.
Figure 6:
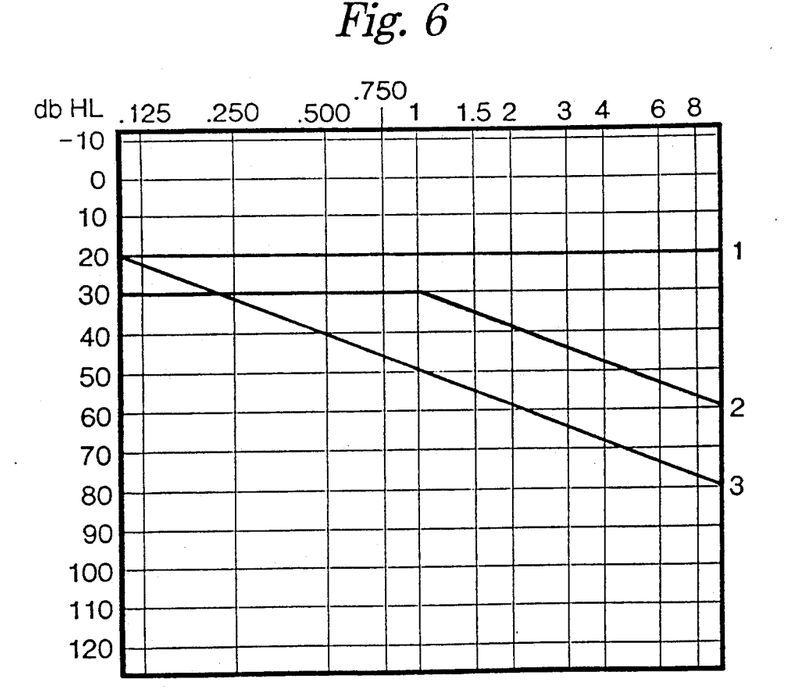
FIG. 6 is a template overlay showing several possible audiogram curve shapes.
Figure 7:
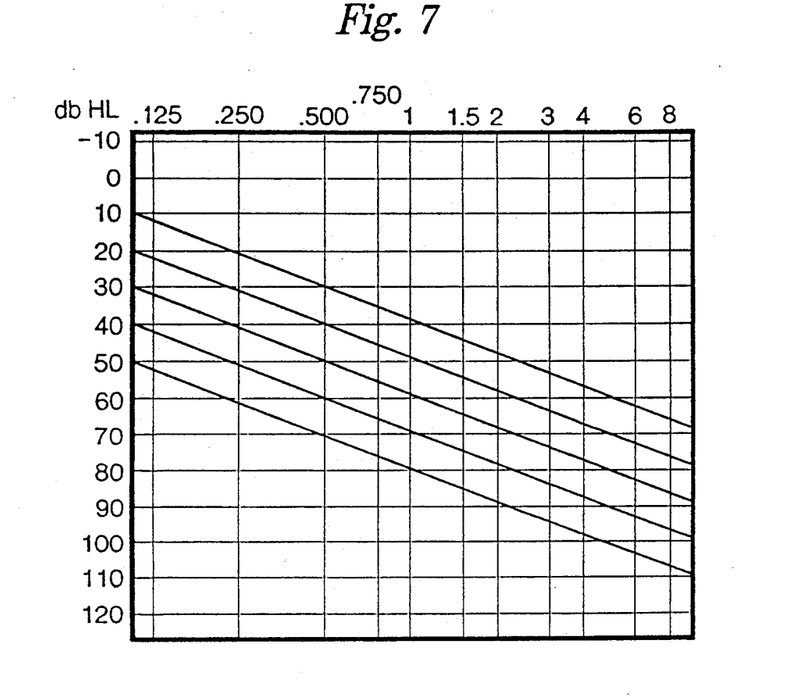
FIG. 7 is a template overlay showing various magnitudes of loss for a patient of type 3 loss (FIG. 6)

The process of deriving the baseline settings used to control the circuit settings shown at 116, 118, 120, 122, and 124 is shown in FIGS. 5–8. In order to derive the data which are used to configure the circuit shown in FIG. 3 the audiologist performs a series of standard tests on the patient. The minimum required to provide an adequate prescription is an audiogram, shown in FIG. 5, and two tests which determine the Most Comfortable Loudness Level (MCL) and the Loudness Discomfort Level (LDL) discussed in Pluvinage's article cited above. While the following procedure is described for only one ear, it should be understood that the same procedure is used for both ears. The audiologist is provided with a set of overlay templates which are laid over the audiogram shown in FIG. 5. These overlays, one of which is shown in FIG. 6, determine both the audiogram curve shape and the magnitude of loss, which are entered in memory 56 using the dip switches. FIG. 6 shows a set of numbered audiogram curve shapes. Most patients audiograms can by categorized into various curve shapes. It is contemplated that the number of curve shapes will be expanded as more test data are produced to more precisely define and expand categories of hearing loss. All the graph shapes shown in FIG. 6 may each be provided with their own template. The audiograms shown in FIG. 5 are representative of numbered graph 3 shown in FIG. 5. Of course, right and left ears may have different types of hearing loss. Once the shape of the audiogram curve has been determined the audiologist uses a second set of overlays to determine the magnitude of hearing loss. This second set is shown in FIG. 7. The overlay represented by FIG. 7 is a series of numbered graph type 3 which vary in magnitude of hearing loss. With this overlay the audiologist determines the magnitude of loss. In the case of the audiogram shown in FIGS. 5 the magnitude of loss is 20 dB. The dip switch settings that comprise memory 56 may correspond to a certain interval in dB, for example a first switch setting may correspond to 5 dB while a second switch setting may correspond to 10 dB. It is contemplated that both the curve shape and magnitude of loss overlays may be combined into one overlay.

Figure 8:
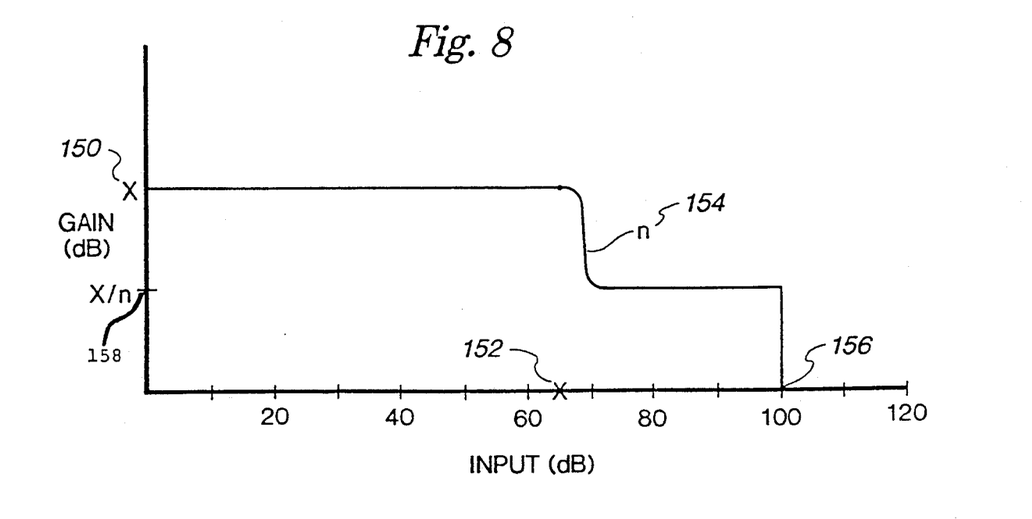
FIG. 8 is a graph of input vs. gain showing the relationship of MCL, LDL and the dynamic range compression constant.

Referring now to FIG. 8 a graph of gain versus input sound is shown. As the level of the input sound increases, a constant gain of X, shown at 150, is maintained. After a certain loudness level however, the patient does not need the input sound amplified as much. At a certain point the gain is reduced to a new, lower level. This point is referred to as the Most Comfortable Level (MCL) and is shown here at 152 as 65 db HL. Reference numeral 154 shows the dynamic range compression constant n which governs what level the gain is eventually reduced to for input louder than 65 db HL. X/n shown at 158 is the final gain level. For example, if n=2 then the gain would be reduced to one half the original level. When the input gets louder than 100 db HL then the Loudness Discomfort Level (LDL, sometimes referred to as UCL) is reached. Amplification after this point is uncomfortable to the patient. After this point, shown at 156, no further amplification takes place. The MCL and LDL numbers used are exemplary only and may vary depending on the particular patient.

The audiologist will next decide which prescription formula to use. There are many choices available, however the two most common choices are POGO (Prescription of Gain/Output) and NAL (National Acoustics Laboratory). The audiologist specifies this choice by using the baseline reference switches which constitute memory 56. These formulas, or a different formula, stored in memory, produce the various baseline settings as discussed above. These settings are used for configuring the hearing aid circuit, as is well known in the art. If the audiologist wishes to use custom settings not derived from a formula, the audiologist may input these settings into the remote control directly by putting the remote control into program mode with a switch (not shown) or a key sequence and then using the keypad as an input device.

During standard testing the audiologist will determine whether or not the patient is a prior hearing aid user. This may also result in a switch setting in memory 56. If the patient is a prior hearing aid user the gain is usually boosted slightly.

The audiologist next sets the switches which control the sensitivity to feedback. At present only three settings are available: high; medium, and low, although it is contemplated that a higher number of settings may be used.

The audiologist then determines the dynamic range compression constant and inputs this using the switches in memory 56.

The following is an example of the dip switch settings expressed in binary code:
Audiogram Curve shape 3 is denoted by switches set to 110;
Magnitude of Loss of 20 dB is denoted by switches set to 010;
Prescription Formula set to NAL is denoted by switches set to 01;
Sensitivity to Feedback set to Medium is denoted by switches set to 01;
Prior Hearing Aid User set to Yes denoted by switch set to 1, and
Dynamic Range Compression Constant of 2 denoted by switches set to 100.

Once the baseline settings are determined the patient may modify the settings by using the remote control 20.

The remote control is provided with volume controls and standard environment keys for automobile; fan; phone; television; music; voice, and restaurant, although it is contemplated that more standard environments may be provided.

To change volume the patient presses either the volume up of volume down key shown at 24 in FIG. 1. The remote control responds by raising or lowering the gains 72 and 86 by between 2 to 5 dB, or some predetermined interval. A further modification of this procedure involves the Maximum Power Output (MPO) which is sent to the hearing aid along with the command to raise the volume. The circuitry is configured to raise the volume only if the volume would not be raised above this MPO level.

This completes the description of the preferred and alternate embodiments of the invention. Those skilled in the art may recognize other equivalents to the specific embodiment described herein which equivalents are intended to be encompassed by the claims attached hereto.

What is claimed is:

1. In combination a hearing aid and apparatus for controlling the hearing aid, comprising:
    the hearing aid comprising:
        a microphone producing a first signal;
        a speaker;
        first circuit means connected between the microphone and the speaker for processing the first signal;
        radiation sensing means for sensing circuit setting data transmitted as radiation from a remote control, the radiation sensing means producing a second signal which corresponds to the circuit setting data transmitted;
        second circuit means for processing the second signal and configuring the first circuit means in accordance with the circuit setting data transmitted by the remote control;
    the remote control comprising:
        a processor;
        memory means holding a computer program;
        memory means for holding baseline reference data, the baseline reference data comprised of a single set of baseline parameters, the baseline parameters providing data to configure the hearing aid for a particular sound environment;
        a keypad containing a plurality of keys corresponding to a plurality of sound environments;
        means for generating circuit setting data, corresponding to a modified set of baseline parameters computed for particular sound environment selected, at the time the sound environment is selected, the circuit setting data computed using the computer program which processes the baseline reference data, and modifies it to configure the hearing air for the sound environment corresponding to the key pressed, based on a key pressed on the keypad, the circuit setting data including all the information required to configure a circuit to a predetermined response;
        a radiation transmitter for transmitting the processed circuit setting data as radiation to the hearing aid;
    whereby when a key on the keypad is pressed the computer program processes the baseline reference data to produce the circuit setting data for a particular sound environment, the remote control transmits the circuit setting data to the hearing aid, which configure the first circuit means in accordance with the circuit setting data.

2. The combination of claim 1 wherein the remote control transmits the circuit setting data using infrared radiation and where the infrared radiation is transmitted substantially perpendicular to the plane defined by the keypad.

3. The combination of claim 2 wherein the hearing aid is powered by a rechargeable lithium battery and where the lithium battery is inductively recharged by a recharger.

4. The combination of claim 2 wherein the hearing aid is powered by a rechargeable nickle-cadmium battery and where the nickel-cadmium battery is inductively recharged by a recharger.

5. The combination of claim 2 further including at least one custom environment sound key which corresponds to a non-standard sound environment.

6. The combination of claim 2 further including a pair of volume control keys constructed and arranged to raise or lower the volume in predetermined increments.

7. The combination of claim 6 wherein the predetermined increment is between 2 and 5 db.

8. The combination of claim 7 wherein pressing the volume control key which raises the volume transmits the maximum power output data which is used in a circuit inside the hearing aid so that the volume will not be raised past the point of maximum power output.

9. In combination a hearing aid and a remote control apparatus for controlling the hearing aid, comprising:
    the remote control apparatus comprising:
        a processor;
        a keypad containing a plurality of keys, each key corresponding to a particular sound environment;
        memory means associated with the processor for storing a computer program and for storing data corresponding to a patient, the data comprised of a single set of baseline parameters, the baseline parameters providing data to the computer program which computes a modified set of parameters to configure the hearing aid for a particular sound environment when a key is pressed, the computer program including a set of formulas which utilize the data of a particular patient to generate a set of circuit settings in a predetermined manner based on a particular key pressed on the keypad, the circuit setting corresponding to a modified set of baseline parameters computed for the particular sound environment selected, at the time the sound environment is selected;
        a control signal transmitter for transmitting a control signal to the hearing aid, the control signal corresponding to the set of circuit settings as computed and modified by the computer program after a key is pressed;
    the hearing aid comprising:
        a microphone producing a first signal in response to sound;
        a speaker for producing sound in response to a processed signal;
        analog circuit means including a plurality of adjustable signal processing circuit element connected between the microphone and the speaker for processing the first signal in a predetermined manner;

control signal sensing means for sensing the control signal transmitted from the remote control;

digital control circuit means connected to the control signal sensing means for adjusting the signal processing circuit elements in accordance with the set of circuit settings transmitted by the remote control;

whereby pressing a key on the remote control causes the control signal, which corresponds to the baseline data as modified by the program, to be transmitted to the hearing aid which adjusts the signal processing circuit elements in accordance with the new circuit settings.

10. The combination of claim 9 wherein the remote control transmits the circuit setting data using infrared radiation and wherein the infrared radiation is transmitted substantially perpendicular to the plane defined by the keypad.

11. The combination of claim 10 wherein the hearing aid is powered by a rechargeable lithium battery and where the lithium battery is inductively recharged by a recharger.

12. The combination of claim 10 wherein the hearing aid is powered by a rechargeable nickle-cadmium battery and where the nickle-cadmium battery is inductively recharged by a recharger.

13. The combination of claim 10 further including at least one custom environment sound key which corresponds to a non-standard sound environment.

14. The combination of claim 10 further including a pair of volume control keys constructed and arranged to raise or lower the volume in predetermined increments.

15. The combination of claim 14 wherein the predetermined increment is between 2 and 5 db.

16. The combination of claim 15 wherein pressing the volume control key which raises the volume transmits the maximum power output data which is used in a circuit inside the hearing aid so that the volume will not be raised past the point of maximum power output.

17. A method of deriving settings for a hearing aid comprising the steps of:

preparing an audiogram of a patient based on standard testing techniques;

determining the most comfortable level of a patient based on standard testing techniques;

determining the loudness discomfort level of a patient based on standard testing techniques;

classifying the patient's hearing loss into a general category by matching the patient's audiogram to a template overlay, where the template comprises a predetermined number of graph shapes;

determining the magnitude of loss by matching the audiogram to a predetermined number of subgraphs contained on a template overly, where the subgraphs vary the magnitude of loss of a particular graph shape;

determining which prescription formula to utilize in calculating the circuit settings for a hearing aid;

determining the dynamic range compression setting, and storing these settings in a remote control whereby these settings are used by the prescription formula to calculate the circuit settings for configuring a hearing aid.

18. The method of claim 17 wherein the graph shape template and the magnitude of loss template are combined into one template.

19. A remotely controlled hearing aid, comprising:

a hearing aid which includes a memory for storing a set of parameters which configure the hearing aid for a particular sound environment;

a remote control which includes:

a first memory fir storing a single set of baseline parameters;

a keyboard including a plurality of keys, each corresponding to a different sound environment;

a second memory for storing a program, and a processor which runs he program to compute a modified set of parameters from he baseline parameters stored in the first memory to provide a set of parameters to configure the hearing aid for the particular sound environment corresponding to the key pressed by a user and wherein the new computed modified set of parameters are computed when the user presses a particular key;

and transmission means for transmitting the newly computed set of parameters to the hearing aid for storage in the memory, whereby the hearing aid is reconfigured in accordance with the new settings for the particular sound environment.

* * * * *

UNITED STATES PATENT AND TRADEMARK OFFICE
CERTIFICATE OF CORRECTION

PATENT NO. : 5,303,306
DATED : April 12, 1994
INVENTOR(S) : Brillhart et al

It is certified that error appears in the above-indentified patent and that said Letters Patent is hereby corrected as shown below:

Col. 12, line 28, delete "fir" and insert --for--
Col. 12, line 33, delete "he" and insert --the--

Signed and Sealed this

Second Day of August, 1994

Attest:

BRUCE LEHMAN

*Attesting Officer*  *Commissioner of Patents and Trademarks*